(12) United States Patent
Coutard et al.

(10) Patent No.: US 11,774,347 B2
(45) Date of Patent: Oct. 3, 2023

(54) PHOTOACOUSTIC DETECTING DEVICE COMPRISING A PROTECTIVE MEMBRANE

(71) Applicant: Commissariat à l'Energie Atomique et aux Energies Alternatives, Paris (FR)

(72) Inventors: Jean-Guillaume Coutard, Grenoble (FR); Alain Gliere, Grenoble (FR); Maryse Fournier, Grenoble (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 17/645,770

(22) Filed: Dec. 23, 2021

(65) Prior Publication Data
US 2022/0205901 A1 Jun. 30, 2022

(30) Foreign Application Priority Data
Dec. 24, 2020 (FR) ...................................... 20 14113

(51) Int. Cl.
*G01N 21/17* (2006.01)
*G01N 33/487* (2006.01)

(52) U.S. Cl.
CPC ....... *G01N 21/1702* (2013.01); *G01N 33/487* (2013.01); *G01N 2201/06113* (2013.01)

(58) Field of Classification Search
CPC ............... G01N 21/1702; G01N 21/03; G01N 21/0303; G01N 21/15; G01N 33/487;
(Continued)

(56) References Cited

U.S. PATENT DOCUMENTS

2005/0090725 A1 4/2005 Page et al.
2014/0073899 A1 3/2014 Cohrs et al.
(Continued)

FOREIGN PATENT DOCUMENTS

WO    WO 2019/081701 A1    5/2019

OTHER PUBLICATIONS

French Preliminary Search Report dated Jul. 26, 2021 in French Application 20 14113 filed on Dec. 24, 2020, 10 pages (with English Translation of Categories of Cited Documents & Written Opinion).

*Primary Examiner* — Suman K Nath
(74) *Attorney, Agent, or Firm* — Oblon, McClelland, Maier & Neustadt, L.L.P.

(57) ABSTRACT

A photoacoustic detecting device to be applied, via a contact face, against a medium to be analyzed, is disclosed. The device includes: a hollow cavity that opens onto a contact aperture, the contact aperture being produced in the contact face; a pulsed or amplitude-modulated light source configured to emit, when activated, an incident light beam, in an emission spectral band, through the cavity, to the contact aperture; and an acoustic transducer connected to the cavity and configured to detect a photoacoustic wave extending through the cavity. Under the effect of illuminating the medium by the incident light beam, the acoustic transducer detects an acoustic wave produced by heating the medium. The cavity includes a membrane extending through the cavity, facing the contact face. The membrane is bounded by a lower face and an upper face. The membrane includes through-apertures produced between the lower face and the upper face.

15 Claims, 4 Drawing Sheets

(58) Field of Classification Search
CPC . G01N 2201/06113; G01N 2021/1706; G01N 2021/0385; G01N 29/2418
See application file for complete search history.

(56) References Cited

U.S. PATENT DOCUMENTS

| | | |
|---|---|---|
| 2015/0051473 A1 | 2/2015 | Huang et al. |
| 2018/0160519 A1* | 6/2018 | Iwamoto ................ H05G 2/008 |
| 2020/0333296 A1 | 10/2020 | Von Lilienfeld-Toal et al. |
| 2021/0139321 A1* | 5/2021 | Patil .................... B23K 26/402 |

* cited by examiner

PHOTOACOUSTIC DETECTING DEVICE COMPRISING A PROTECTIVE MEMBRANE

TECHNICAL FIELD

The technical field of the invention is detection of an analyte via photoacoustic detection.

PRIOR ART

Photoacoustic detection is based on detection of an acoustic wave generated under the effect of absorption, by an analysed medium, of a pulsed or amplitude-modulated incident electromagnetic wave. The acoustic wave is formed following heating of molecules of interest, which are present in the analysed medium, under the effect of absorption of the incident wave. The heating leads to a modulated thermal expansion of the medium, said expansion being the origin of the acoustic wave.

Photoacoustic detection may be made specific to one particular analyte, by adjusting the wavelength of the incident electromagnetic wave to a wavelength of absorption of the analyte. Photoacoustic detection has thus been applied to detect gas species in a gas, or to detect the presence of particular molecules in biological tissues. The wavelength of the incident wave is frequently located in the infrared.

Photoacoustic detection is then a non-invasive analysis technique, able to be applied to scattering or opaque media.

Applications of photoacoustic detection to biological tissues are described in the following publications:

Bauer A J. "IR-spectroscopy for skin in vivo: optimal skin sites and properties for non-invasive glucose measurement by photoacoustic and photothermal spectroscopy"; Journal of Biophotonics 11 (2018);

"Windowless ultrasound photoacoustic cell for in-vivo mid-IR spectroscopy of human epidermis: Low interference by changes of air pressure, temperature, and humidity caused by skin contact opens the possibility for a non-invasive monitoring of glucose in the interstitial fluid", Rev. Sci. Instrum. 84, 084901 (2013).

In these publications, an aptitude-modulated laser light source activated at a frequency comprised between several tens of Hz and several tens of kHz is used. The objective is to estimate a concentration of glucose in interstitial bodily fluid, at a depth comprised between 10 µm and 100 µm under the surface of the skin of a user. To do this, a photoacoustic detecting device placed against the skin of a user is used.

A photoacoustic detecting device comprises a transducer, configured to detect an amplitude-modulated acoustic wave under the effect of periodic heating induced by the modulated light wave. More precisely, the photoacoustic detecting device is arranged to detect a periodic pressure modulation, with a period depending on the modulation frequency of the light wave. A response function of the photoacoustic device may be calibrated, so as to establish a correlation between the measured pressure modulation and the amount of analyte present in the analysed medium.

A difficulty may arise because of water vapour emanating from the skin, as a result of sweating. The water vapour may condense and form droplets, which may damage the transducer. Moreover, during use of the device, dust, or other undesirable elements, for example skin debris, may accumulate in the device. The objective of the invention is to solve this problem.

DISCLOSURE OF THE INVENTION

A first subject of the invention is a photoacoustic detecting device intended to be applied, via a contact face, against a medium to be analysed, the device comprising:

a hollow cavity that opens onto a contact aperture, the contact aperture being produced in the contact face;

a pulsed or amplitude-modulated light source configured to emit, when it is activated, an incident light beam, in an emission spectral band, through the cavity, to the contact aperture;

an acoustic transducer connected to the cavity, and configured to detect an acoustic wave extending through the cavity;

such that, under the effect of an illumination of the medium by the incident light beam, the acoustic transducer detects an acoustic wave produced by heating of the medium;

wherein:

the cavity comprises a membrane extending through the cavity, facing the contact face;

the membrane is bounded by a lower face and an upper face, the membrane comprising through-apertures produced between the lower face and the upper face.

By through-aperture, what is meant is an aperture allowing air to pass through the aperture, between the lower face and the upper face of the membrane.

The device may comprise any of the features described below, alone or in technically achievable combinations.

The radius of each through-aperture is comprised between 5 µm and 25 µm.

The membrane defines an aperture factor, corresponding to a ratio of a cumulative area of each through-aperture to the total area of the lower face or of the upper face of the membrane, the aperture factor for example being comprised between 0.05 and 0.3.

The thickness of the membrane is comprised between 100 µm and 1 mm.

The membrane lies inside the cavity, at a nonzero distance from the contact face.

Advantageously:

the membrane is arranged such that, when the light source is activated, the incident light beam passes through the membrane before reaching the contact aperture;

the membrane comprises an intersection section, corresponding to a portion of the membrane passed through by the light beam;

at least in the intersection section, the membrane is made of a transparent material, having a transmittance, in the emission spectral band, higher than 0.4, and preferably higher than 0.8.

The membrane may be unapertured in the intersection section. By unapertured, what is meant is without any through-apertures.

The transparent material may consist of at least one material chosen from: Si, Ge, AlN, ZnSe, $BaF_2$, $CaF_2$, KBr, ZnS, sapphire.

At least in the intersection section, the upper face of the membrane may comprise an antireflective coating.

The antireflective coating may be applied to all of the upper face, and optionally to all or some of the lower face.

According to one possibility, the membrane is monolithic. It is manufactured from a single material (neglecting any optional hydrophobic coating or antireflective coating).

According to one possibility, the membrane is made:

of a first material outside of the intersection section;

of an auxiliary material, forming said transparent material, in the intersection section.

The membrane may comprise a hydrophobic coating, notably on the lower face.

According to one embodiment,
- the cavity is bounded by a transverse wall and a lateral wall, the lateral wall extending between the transverse wall and the contact face;
- the membrane extends between two opposite faces of the lateral wall.

The transverse wall may be parallel to the contact face.

According to one embodiment, the membrane is placed removably in the cavity.

The light source may be a laser source.

The volume of the cavity may be smaller than 50 μL.

The invention will be better understood on reading the description of examples of embodiment, which are presented, in the rest of the description, with reference to the figures listed below.

FIGURES

FIG. 1A shows one embodiment of a photoacoustic detecting device.

FIG. 1B schematically shows a separation of the cavity of the device into a lower cavity and an upper cavity.

FIG. 1C schematically shows a membrane.

FIG. 2 shows a transmission function, taking into account reflection at the interfaces, of a silicon membrane of 300 μm thickness.

FIG. 3 schematically shows a droplet formed on the lower surface of the membrane and penetrating into a through-aperture in the membrane.

FIG. 4A shows a modelled cavity, in which a membrane separates a lower cavity and an upper cavity.

FIG. 4B schematically shows an equivalent circuit diagram of the modelled cavity of FIG. 4A.

Figure 5A:
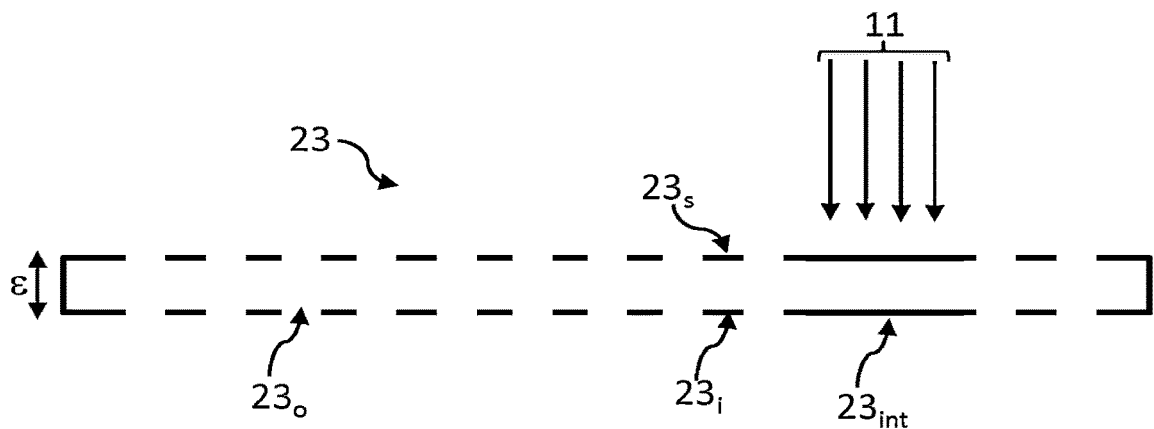
FIG. 5A shows a variant in which the membrane comprises an unapertured portion, in an intersection section corresponding to a section of the membrane passed through by an incident light beam.
Figure 5B:
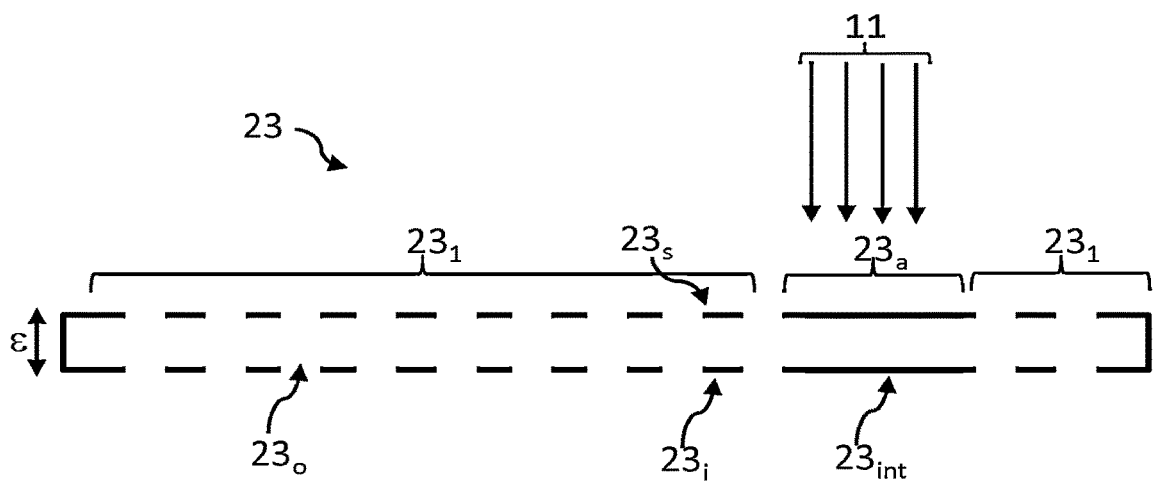

FIG. 5B schematically shows a variant in which the membrane is a composite membrane, formed by a "standard" material that is not necessarily transparent in the infrared, and an auxiliary material, which is transparent in the infrared, the latter being placed in the intersection section.

SUMMARY OF PARTICULAR EMBODIMENTS

Figure 1A:
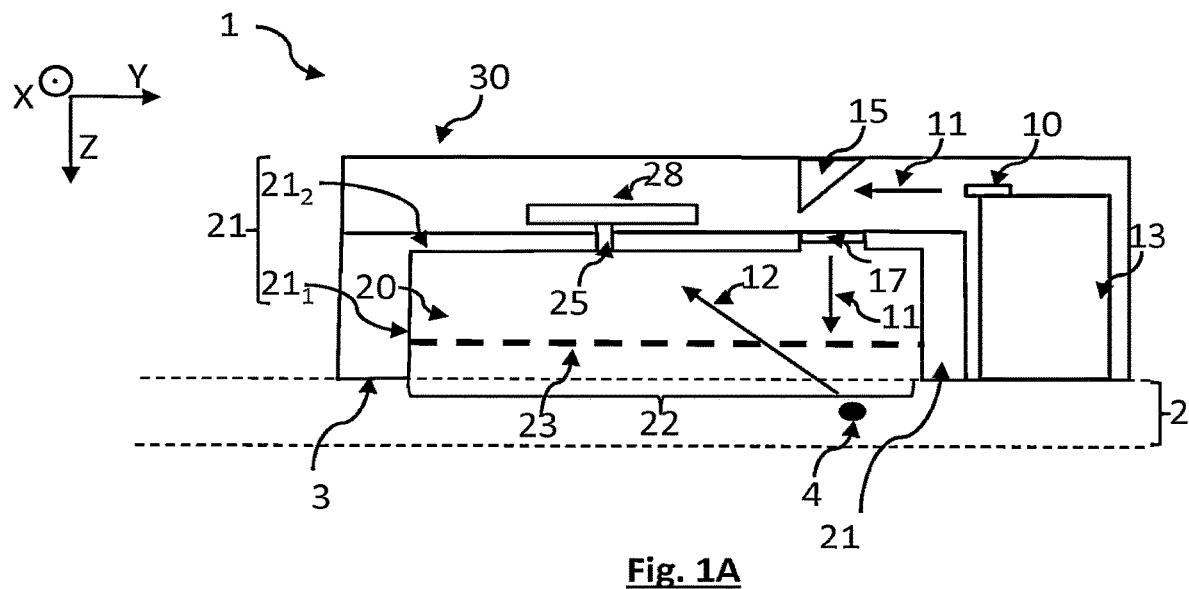

FIG. 1A schematically shows a device 1 allowing the invention to be implemented. The device 1 is configured to be applied against a medium 2 to be analysed. The device comprises a contact face 3, which is intended to be applied against the medium to be analysed. The contact face is designed to conform to the medium against which it is intended to be pressed. It is for example planar.
In this example, the medium 2 is the skin of a user. The device comprises a light source 10, configured to emit a light beam 11 that propagates to the medium 2 to be analysed. The light source 10 is pulsed or amplitude-modulated. The light beam 11 is emitted in an emission spectral band Δλ comprising an absorption wavelength $\lambda_a$ of an analyte 4 present in the medium. One objective of the device 1 is to detect the presence of the analyte 4 and optionally to estimate a concentration thereof.

The analyte 4 may be a molecule present in a bodily fluid. It may for example be a question of glucose, or of a bodily analyte such as cholesterol, triglycerides, urea, albumin, alcohol (for example ethanol), tetrahydrocannabinol.

The emission spectral band preferably lies in the visible or in the infrared, and for example between wavelengths of 3 μm and 15 μm. Preferably, the emission spectral band Δλ is sufficiently narrow, so that the device 1 is specific to a single analyte. When the analyte is glucose, the emission spectral band is centred on an absorption wavelength of glucose, which for example corresponds to a wave number of 1034 cm$^{-1}$. The light source 10 may notably be a pulsed laser source, for example a wavelength-tunable quantum cascade laser (QCL). The emission spectral band Δλ is then located in the infrared.

According to other embodiments, the light source may be a filament-based source, or a light-emitting diode. According to these embodiments, it is preferable to associate the light source with a bandpass filter so as to define a sufficiently narrow emission spectral band centred on the absorption wavelength in question. However, use of a laser source is preferred.

In the embodiment shown in FIG. 1A, the device 1 comprises an optical component 15, which is configured to steer the light beam 11 emitted by the light source toward the medium 2 to be analysed.

The device 1 is intended to be applied against the medium to be analysed 2. It comprises a confining jacket 21, which is placed in contact with the medium, and which bounds a cavity 20. The cavity 20 opens onto a contact aperture 22, which is produced in the contact face 3, so as to open onto the medium 2. The light beam 11, after having been reflected by the optical component 15, propagates to the medium 2 through the cavity 20, and through the contact aperture 22. The device comprises a transparent window 17, which is configured to transmit the incident light beam 11.

In the device shown in FIG. 1A, the optical component 15 is a reflector, taking the form of a reflective prism. Preferably, the incident light beam 11 reaches the medium 2 at normal incidence, or substantially normal incidence. By substantially normal, what is meant is normal to within an angular tolerance of ±30°.

Under the effect of the presence of an analyte 4 in the medium 2, an acoustic wave, called the photoacoustic wave 12, is formed. The photoacoustic wave 12 is an acoustic wave formed as a result of periodic heating of the medium by the incident light beam 11, the latter being pulsed or amplitude-modulated. One portion of the photoacoustic wave 12 extends through the cavity 20 so as to be detected by an acoustic transducer 28. The acoustic transducer 28 is connected to the cavity 20 by an acoustic channel 25. The acoustic transducer may be a microphone, having a detection spectral range comprising the frequency of the photoacoustic wave. The photoacoustic wave is amplitude-modulated at the pulse frequency or amplitude-modulation frequency of the light source. Thus, at the transducer, the pressure is amplitude-modulated.

The confining jacket 21 comprises:
- a lateral component $21_1$, preferably extending parallel to an axis Z normal to the contact face 3. The lateral component $21_1$ forms a lateral wall bounding the cavity.
- a transverse component $21_2$ extending parallel, or substantially parallel, to the contact face 3, facing the latter. The transverse component $21_2$ extends parallel, or substantially parallel, to the contact aperture 22. In the embodiment shown in FIG. 1A, the transverse component $21_2$ includes the window 17. The transverse component $21_2$ forms a transverse wall bounding the cavity.

By substantially parallel, what is meant is parallel to within an angular tolerance of ±30° or ±20°.

The lateral face $21_1$ extends between the contact face 3 and the transverse face $21_2$.

The device comprises a protective cover 30, jacketing the components described above. The light source is placed on a carrier 13, which is connected to the cover 30.

As mentioned in the publication Kottmann "Mid-infrared photoacoustic detection of glucose in human skin: towards non-invasive diagnostics", Sensors 2016, 16, 1663, a relationship may be established between the modulation amplitude A of the photoacoustic wave, at the modulation frequency f, and the volume V of the cavity 20, such that:

$$A \propto \frac{I_{11}(\lambda)\alpha(\lambda)}{Vf^{\frac{3}{2}}} \quad (1)$$

where:
- ∝ is the proportional operator;
- $I_{11}(\lambda)$ is the intensity of the incident light beam at the wavelength A;
- α(A) is an absorption coefficient of the analysed medium at the wavelength A;
- V is the volume of the cavity, potentially including the acoustic channel;
- f is the modulation frequency of the acoustic wave.

When the frequency f and the intensity $I_{11}(\lambda)$ of the light beam are set, the modulation amplitude A of the photoacoustic wave detected by the acoustic transducer is proportional to the absorption coefficient α(λ) of the medium. However, the latter is considered to be proportional to the concentration of analyte in the medium. Thus, measuring modulation amplitude A with the acoustic transducer 28 allows the concentration of analyte 4 in the medium to be estimated, by taking into account the absorption coefficient α(λ) of the medium.

Figure 1B:
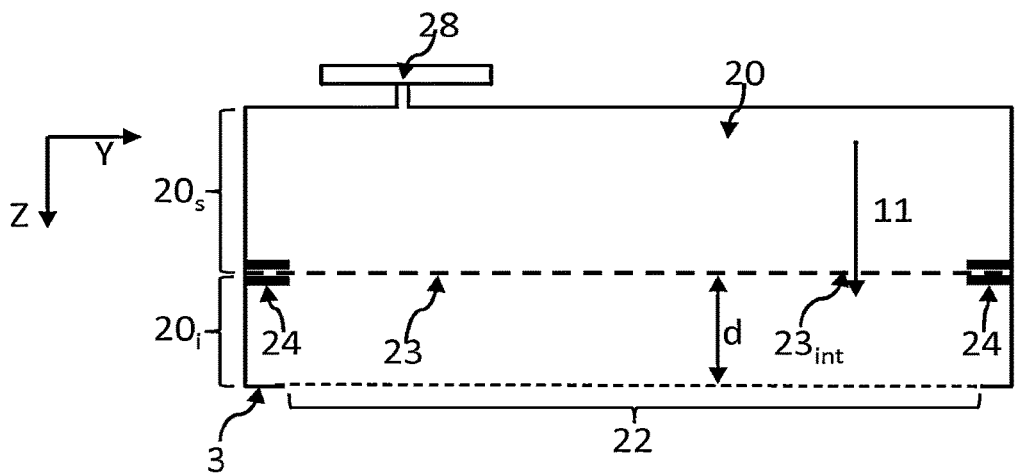

The device comprises a membrane 23, lying, inside the cavity 20, between the contact face 3 and the transducer 28. As illustrated in FIG. 1B, the membrane 23 allows the cavity to be sectioned between:
- a lower cavity $20_i$, extending between the contact face 3 and the membrane 23;
- an upper cavity $20_s$, extending between the membrane 23 and the transducer 28.

Thus, the membrane forms a protective screen, interposed between the lower cavity $20_i$ and the upper cavity $20_s$. This allows the upper cavity $20_s$ to be isolated from water droplets or dust, or other undesirable elements liable to be present in the lower cavity $20_i$, having entered the latter through the contact aperture 22.

The membrane 23 lies inside the cavity 20, at a nonzero distance d from the contact aperture 22. Specifically, during the implementation of the device, it is preferable for the membrane 23 not to make contact with the skin 2, in order not to disrupt heating of a surface layer of gas in contact with the skin 2. Placing the membrane at a distance allows a layer of air to be kept between the contact aperture 22 and the membrane. The distance between the membrane and the contact aperture is preferably larger than 200 μm, or 500 μm.

The membrane preferably extends right through the cavity, facing the contact face 3. It extends between opposite points of the lateral face. The membrane is preferably placed parallel to the contact face, or substantially parallel to the latter.

The membrane 23 is held inside the cavity 20 by a holder 24. In this example, the membrane is inserted into the holder 24. The membrane 23 may be removable, this allowing the latter to be replaced and/or cleaned.

When the light source 10 is activated, the light beam 11 passes through the membrane 23 before reaching the contact aperture 22. The membrane comprises an intersection section $23_{int}$, corresponding to the portion of the membrane passed through by the light beam 11.

At least in the intersection section $23_{int}$, the membrane is formed from a material having a high transmittance in the spectral band Δλ of the emitted beam 11. By high transmittance, what is meant is that the material has a transmittance that is preferably higher than 0.4 or even and preferably higher than 0.8, and for example of the order of 0.9 or more. The material may for example be silicon. By transmittance, what is meant is a fraction of the light intensity transmitted by the membrane 23. The membrane may be partially or entirely formed from Si, or another material transparent in the infrared, for example porous Si, Ge, AlN, ZnSe, $BaF_2$, $CaF_2$, KBr, ZnS, or sapphire.

Figure 2:
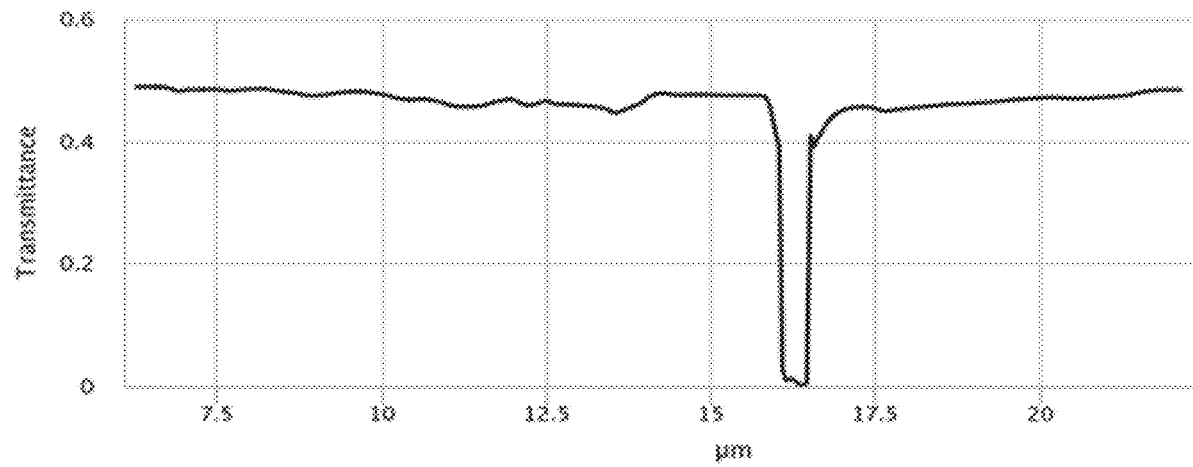

FIG. 2 shows the transmittance (y-axis), as a function of wavelength (x-axis—units μm), of an Si membrane of 300 μm thickness. The transmittance is affected by reflections, notably from the upper face $23_s$. The transmittance may be enhanced, to achieve values close to 1, by applying an antireflective coating, in particular to the upper face $23_s$, and preferably to the upper face $23_s$ and to the lower face $23_i$. The antireflective coating may take the form of a "quarter-wave" plate, deposited in the form of a thin layer. The thin layer may be deposited on all or some of the upper face (and preferably of the lower face), without running the risk of blocking the through-apertures, because of the small thickness of the thin layer.

The membrane may also be composite, comprising a material considered to be sufficiently transparent in the infrared in the intersection section $23_{int}$, and another material outside of the intersection section. One example of a composite membrane is described below with reference to FIG. 5B.

Figure 1C:
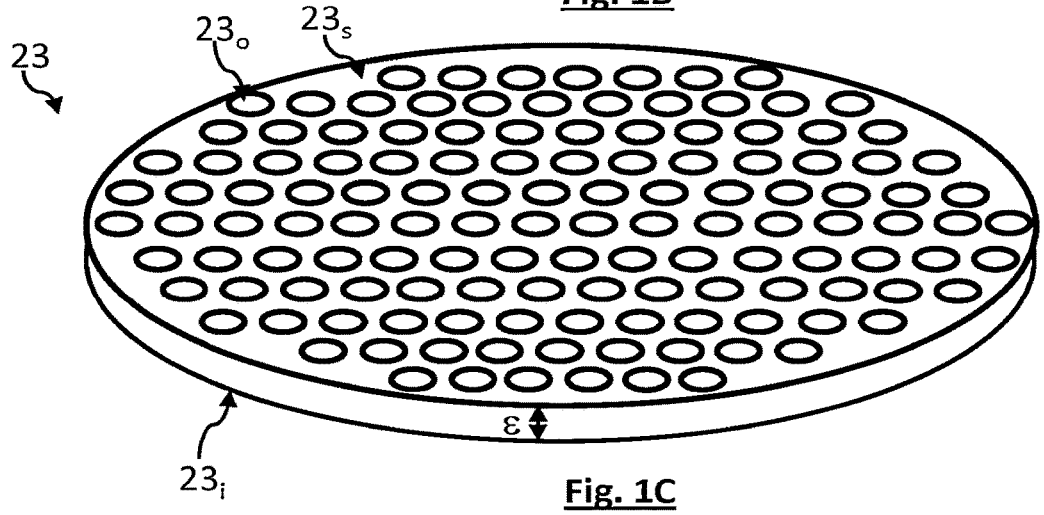

In order to allow the pressure modulations to be transmitted through the cavity 20, to the transducer 28, the membrane comprises through-apertures $23_o$, which extend right through the thickness of the membrane. The through-apertures are shown in FIG. 1C. The through-apertures are dimensioned to transmit the pressure modulation through the membrane 23, while blocking droplets of liquid or dust. These through-apertures 23 allow a communication of air between the lower cavity $20_i$ and the upper cavity $20_s$.

Figure 3:
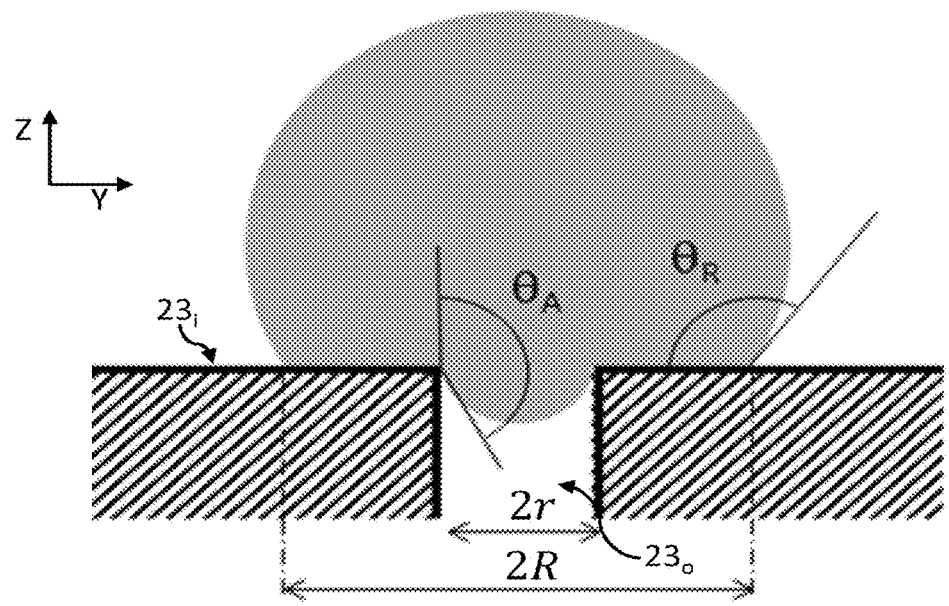

FIG. 3 shows a droplet deposited on the lower face $23_i$ of the membrane 23. Wetting angles $\theta_R$ and $\theta_A$ of the droplet on the lower face of the membrane and in a through-aperture $23_o$, respectively, have been shown. A microdroplet, which may form by condensation of water vapour resulting from sweating, is considered here. The droplet being assumed to be microscopic, capillary forces predominate over gravitional forces. The droplet is subjected to a pressure difference, i.e. a different pressure on either side of the membrane, due to antagonistic capillary forces, which interact with the droplet via the lower face $23_i$, and via the through-aperture $23_o$. These capillary forces induce a pressure difference Δp to which the droplet is subjected, and which may be expressed by:

$$\Delta p = -2\gamma \cos(\theta_A)/r + 2\gamma \cos(\theta_R)/R \quad (2)$$

where
- γ: is the liquid/air surface tension; when the liquid is water, γ=0.073 N/m; when the liquid is a biological buffer, more representative of sweat, γ=0.03 N/m
- r: is the radius of the through-aperture $23_o$;
- R: is the radius of the line wetted on the lower face $23_i$.

Expression (2) was sourced from Cho, H.-Y. Kim, J. Y. Kang, and T. S. Kim, "How the capillary burst microvalve works", *J. Colloid Interface Sci.*, vol. 306, n° 2, p. 379-385, February 2007. Expression (2) defines a condition of penetration of the droplet into a through-aperture of circular cross section. The membrane blocks the droplet when Δp>0.

The droplet forms a meniscus, which engages in the through-aperture $23_o$, and is subjected to capillary forces that tend to make the droplet progress through the interior of a capillary tube formed by the through-aperture. The resultant pressure is $$-2\gamma \frac{\cos(\theta_A)}{r}.$$

A residual portion of the droplet is retained on the lower face $23_i$, and is subjected to capillary forces. The resultant pressure is $$2\gamma \frac{\cos(\theta_R)}{R}.$$

In order to increase the wetting angle $\theta_R$, it is possible to apply a hydrophobic surface treatment to the lower face $23_i$ of the membrane. Specifically, when the material forming the membrane is Si, which is a hydrophilic material, the wetting angle for water is 5°. When a droplet of a biological buffer is considered, this better approximating the conditions encountered when the device is applied to the skin of a user, the wetting angle is of the order of 20° to 40°. The application of a hydrophobic surface treatment, for example a silanization (grafting of hydrophobic silane functions), allows the wetting angle to be increased to 110° for water and 80° for the biological buffer. A hydrophobic surface treatment thus enhances the capacity to retain the droplet on the lower face of the membrane. The hydrophobic treatment may also "overflow" onto the internal surface of the through-apertures.

Apart from the wettability of the liquid, the surface tension γ is also a key parameter. When the diameter of a through-aperture $23_o$ is equal to 20 μm (r=10 μm), and the liquid is water (γ=0.073 N/m) or biological liquid (γ=0.03 N/m), application of expression (1) leads to Δp=0.14 bar and Δp=0.06 bar, respectively. It is therefore necessary to apply a pressure higher than Δp for the droplet to pass through the membrane by capillarity. This estimation was carried out considering R=20 μm.

The radius of the through-apertures is preferably comprised between 5 μm and 25 μm, and preferably between 5 μm and 15 μm. When the radius increases, the transmission of the pressure modulations is optimal, but the value Δp decreases: the membrane is less able to block passage of droplets through the through-apertures. This drawback may, to a certain extent, be overcome by applying a hydrophobic surface treatment to the lower face $23_i$.

The thickness ε of the membrane 23 is preferably comprised between 100 μm and 1 mm, and preferably between 150 μm and 750 μm.

The radius of each through-aperture also depends on the thickness ε of the membrane. The through-apertures may be formed, in an Si substrate, by photolithography followed by wet etching. In this case, it is considered that through-apertures the diameter of which is of the order of one tenth of the thickness ε, or even less if necessary, may be formed.

The membrane is dimensioned to allow the pressure modulation to be transmitted between the lower and upper portions of the cavity. The number of through-apertures must be determined so that the effect of the membrane on the photoacoustic wave may be considered to be negligible, in the frequency range corresponding to the pulse frequency of the light source.

Figure 4A:
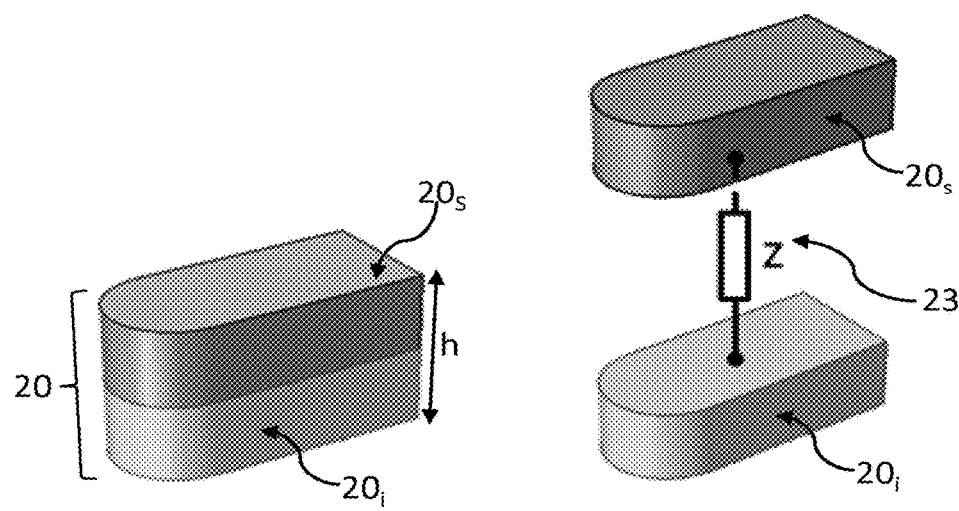
FIG. 4C shows an amplitude of modulation of the pressure in the lower cavity and in the upper cavity taking into account two aperture factors of the membrane.
Figure 4B:
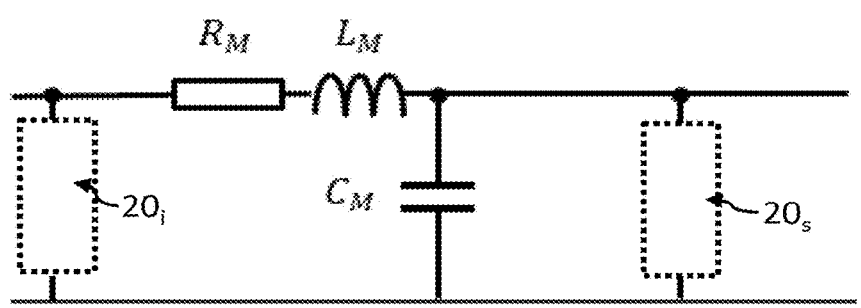

The aperture factor of the membrane corresponds to a ratio between the cumulative area of each through-aperture and the total area of the lower face (or of the upper face). The aperture factor may be comprised between 0.01 and 0.3. The inventors have modelled the transmission of the amplitude modulations of the photoacoustic wave 12 for two aperture factors. The model was generated considering the membrane to form an acoustic impedance analogous to an electrical impedance. FIG. 4A shows the modelled cavity 20 (left-hand figure), the membrane 23, which is placed at mid-height, forming an acoustic impedance that is comparable to an electrical impedance Z (right-hand figure). The acoustic impedance was modelled by an RLC circuit such as shown in FIG. 4B. The membrane is comparable to a circuit $R_M$, $L_M$, $C_M$, between the lower cavity $20_i$ and the upper cavity $20_s$.

The modelled cavity had a volume of 4.45 mm³ and a height h of 1.5 mm. Two different aperture factors were considered:
- a first aperture factor, corresponding to 1000 through-apertures of 10 μm radius: the value of the first aperture factor was 0.1;
- a second aperture factor, corresponding to 100 through-apertures of 10 μm radius: the value of the second aperture factor was 0.01.

The thickness of the modelled membrane was 200 μm.

Figure 4C:
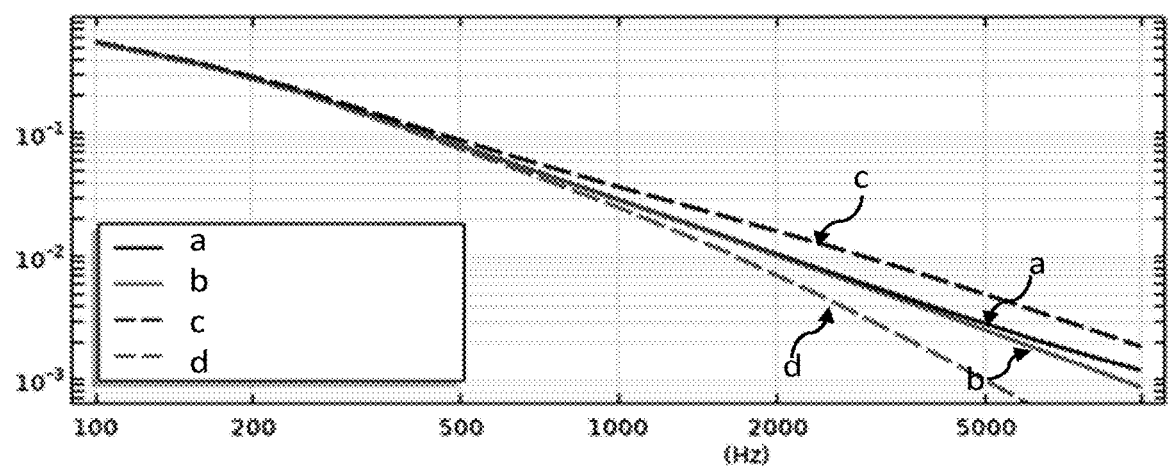

FIG. 4C shows the amplitude of a modulation of pressure (y-axis—arbitrary units) as a function of modulation frequency (x-axis—Hz):
- considering the first aperture factor, in the lower cavity $20_i$ (curve a—solid black line) and in the upper cavity $20_s$ (curve b—solid grey line);
- considering the second aperture factor, in the lower cavity $20_i$ (curve c—dashed black line) and in the upper cavity $20_s$ (curve d—dashed grey line).

FIG. 4C shows the effect of aperture factor on the transmission of the pressure modulation from one side of the membrane to the other. It may be seen that the lower, second aperture factor leads to an attenuation of the pressure modulation transmitted by the membrane, in particular at high frequencies.

In order to prevent the transmission of the light beam 11 from being subjected to diffraction effects, the intersection section $23_{int}$ of the membrane may be unapertured, as shown in FIG. 5A. The unapertured section may comprise an antireflective coating, applied to the upper face $23_s$ and preferably also to the lower face $23_i$. The antireflective coating may be a thin layer or a photonic crystal. By unapertured section, what is meant is a section containing no through-apertures.

The membrane may be monolithic, i.e. formed from a single material, neglecting any optional antireflective treatment or any optional hydrophobic treatment. FIG. 5B shows one variant, in which the membrane is a composite membrane. The membrane is composed of a standard first material $23_1$, which is not necessarily transparent in the infrared, outside of the intersection section. In the intersection section, the membrane comprises an auxiliary material $23_a$, which is transparent in the infrared. The first material $23_1$ may be that of a standard porous membrane, for example a material such as GoreTex (registered trademark). The auxiliary material $23_a$ is different from the first material $23_1$.

The invention claimed is:

1. A photoacoustic detecting device configured to be applied, via a contact face, against a medium to be analysed, the device comprising:
    a hollow cavity that opens onto a contact aperture, the contact aperture being formed in the contact face;
    a pulsed or amplitude-modulated light source configured to emit, when the light source is activated, an incident light beam, in an emission spectral band, through the cavity, to the contact aperture; and
    an acoustic transducer connected to the cavity, and configured to detect an acoustic wave extending through the cavity so that, under an effect of an illumination of the medium by the incident light beam, the acoustic transducer detects an acoustic wave produced by heating of the medium with the incident light beam,
    wherein:
        the cavity comprises a membrane extending through the cavity, facing the contact face;
        the membrane is bounded by a lower face and an upper face, the membrane comprising through-apertures produced between the lower face and the upper face; and
        the membrane lies inside the cavity, at a nonzero distance from the contact face so that an air layer lies between the membrane and the contact face.

2. The device according to claim 1, wherein a radius of each through-aperture is comprised between 5 μm and 25 μm.

3. The device according to claim 1, wherein:
    the membrane defines an aperture factor, corresponding to a ratio of a cumulative area of each through-aperture to the total area of the lower face or of the upper face of the membrane; and
    the aperture factor is comprised between 0.05 and 0.3.

4. The device according to claim 1, wherein a thickness of the membrane is comprised between 100 μm and 1 mm.

5. The device according to claim 1, wherein:
    the membrane is configured such that, when the light source is activated, the incident light beam passes through the membrane before reaching the contact aperture;
    the membrane comprises an intersection section, corresponding to a portion of the membrane passed through by the light beam; and
    at least in the intersection section, the membrane is made of a transparent material, having a transmittance, in the emission spectral band, higher than 0.4.

6. The device according to claim 5, wherein the membrane is unapertured in the intersection section.

7. The device according to claim 5, wherein the transparent material consists of at least one material chosen from: Si, Ge, AlN, ZnSe, $BaF_2$, $CaF_2$, KBr, ZnS, and sapphire.

8. The device according to claim 5, wherein at least in the intersection section, the upper face of the membrane comprises an antireflective coating.

9. The device according to claim 5, wherein the membrane is made:
    of a first material outside of the intersection section; and
    of an auxiliary material, forming said transparent material, in the intersection section.

10. The device according to claim 1, wherein the membrane comprises a hydrophobic coating on the lower face.

11. The device according to claim 1, wherein:
    the cavity is bounded by a transverse wall and a lateral wall, the lateral wall extending between the transverse wall and the contact face; and
    the membrane extends between two opposite faces of the lateral wall.

12. The device according to claim 1, wherein the membrane is placed removably in the cavity.

13. The device according to claim 1, wherein the light source is a laser source.

14. The device according to claim 1, wherein the volume of the cavity is smaller than 50 μL.

15. The device according to claim 1, wherein the distance between the membrane and the contact aperture is larger than 200 μm.

* * * * *